US010335565B2

(12) United States Patent
Johnson et al.

(10) Patent No.: US 10,335,565 B2
(45) Date of Patent: *Jul. 2, 2019

(54) MEASURING RESPIRATORY MECHANICS PARAMETERS OF VENTILATED PATIENTS

(71) Applicants: Arthur T. Johnson, Darlington, MD (US); Jafar Vossoughi, Brookeville, MD (US)

(72) Inventors: Arthur T. Johnson, Darlington, MD (US); Jafar Vossoughi, Brookeville, MD (US)

( * ) Notice: Subject to any disclaimer, the term of this patent is extended or adjusted under 35 U.S.C. 154(b) by 783 days.

This patent is subject to a terminal disclaimer.

(21) Appl. No.: 14/815,442

(22) Filed: Jul. 31, 2015

(65) Prior Publication Data
US 2016/0038697 A1 Feb. 11, 2016

Related U.S. Application Data

(60) Provisional application No. 62/033,503, filed on Aug. 5, 2014.

(51) Int. Cl.
*A61M 16/00* (2006.01)
*A61B 5/085* (2006.01)
(Continued)

(52) U.S. Cl.
CPC ......... *A61M 16/0006* (2014.02); *A61B 5/085* (2013.01); *A61B 5/09* (2013.01);
(Continued)

(58) Field of Classification Search
CPC ........... A61B 5/08; A61B 5/085; A61B 5/087; A61B 5/091; A61B 5/097
See application file for complete search history.

(56) References Cited

U.S. PATENT DOCUMENTS 6,066,101 A 5/2000 Johnson et al.
9,895,082 B2 2/2018 Johnson et al.
(Continued)

OTHER PUBLICATIONS

Lausted et al., "Respiratory resistance measured by an airflow perturbation device", IOP Publishing Ltd, 1999, pp. 21-35.
(Continued)

*Primary Examiner* — Puya Agahi
(74) *Attorney, Agent, or Firm* — Edell, Shapiro & Finnan, LLC

(57) ABSTRACT

An airflow perturbation device for measuring respiratory resistance of a patient breathing with the use of a ventilator comprises a sealed housing having a first port and a second port each configured to couple to a ventilator hose, a perturbation mechanism to periodically alter air flow resistance between the first port and the second port, a pneumotachometer comprising a flow sensor to measure airflow between the first port and the second port, a pressure sensor to measure a difference in air pressure between the first port and the second port, and a computing system comprising at least one processor configured to receive data from the flow sensor and pressure sensor. The computing system determines an airflow resistance based on the received data. Embodiments of the present invention further include a method and computer program product for measuring respiratory resistance of a ventilated patient in substantially the same manners described above.

19 Claims, 6 Drawing Sheets

(51) Int. Cl.
　　　*A61B 5/09*　　　(2006.01)
　　　*A61B 5/08*　　　(2006.01)
　　　*A61B 5/091*　　(2006.01)
　　　*A61B 5/087*　　(2006.01)
　　　*A61B 5/097*　　(2006.01)

(52) U.S. Cl.
　　　CPC ................ *A61B 5/08* (2013.01); *A61B 5/087* (2013.01); *A61B 5/091* (2013.01); *A61B 5/097* (2013.01); *A61M 2016/0027* (2013.01); *A61M 2016/0036* (2013.01); *A61M 2205/103* (2013.01); *A61M 2205/3584* (2013.01); *A61M 2205/502* (2013.01); *A61M 2230/46* (2013.01)

(56) References Cited

U.S. PATENT DOCUMENTS

| | | |
|---|---|---|
| 2009/0301486 A1 | 12/2009 | Masic |
| 2011/0273299 A1 | 11/2011 | Milne |
| 2011/0282228 A1 | 11/2011 | Shiner |
| 2016/0038056 A1 | 2/2016 | Johnson et al. |
| 2016/0038057 A1 | 2/2016 | Johnson et al. |

OTHER PUBLICATIONS

Johnson et al., "Perturbation Device for Noninvasive Measurement of Airway Resistance", Medical Instrumentation 8(2), Mar. 1974.

Johnson et al., "Validation of Airflow Perturbation Device Resistance Measurements in Excised Sheep Lungs", Institute of Physics Publishing, Physiological Measurement, May 10, 2004, pp. 679-690.

Johnson et. al., "Airflow Perturbation Device for Measuring Airways Resistance of Humans and Animals", IEEE Transactions on Biomedical Engineering, vol. BME-31, No. 9, Sep. 1984, pp. 622-626.

Coursey et al., "Comparison of Expiratory Isovolume Pressure-Flow Curves With the Stop-Flow Versus the Esophageal-Balloon Method", Respiratory Care, Jul. 2011, vol. 56, No. 7, pp. 969-975.

Tobin, "Ventilator Monitoring, and Sharing the Data with Patients", American Journal of Respiratory and Critical Care Medicine, vol. 163, 2001, pp. 810-811.

Johnson et al., "Variation of Respiratory Resistance Suggests Optimization of Airway Caliber", IEEE Transactions on Biomedical Engineering, vol. 59, No. 8, Aug. 2012, pp. 2355-2361.

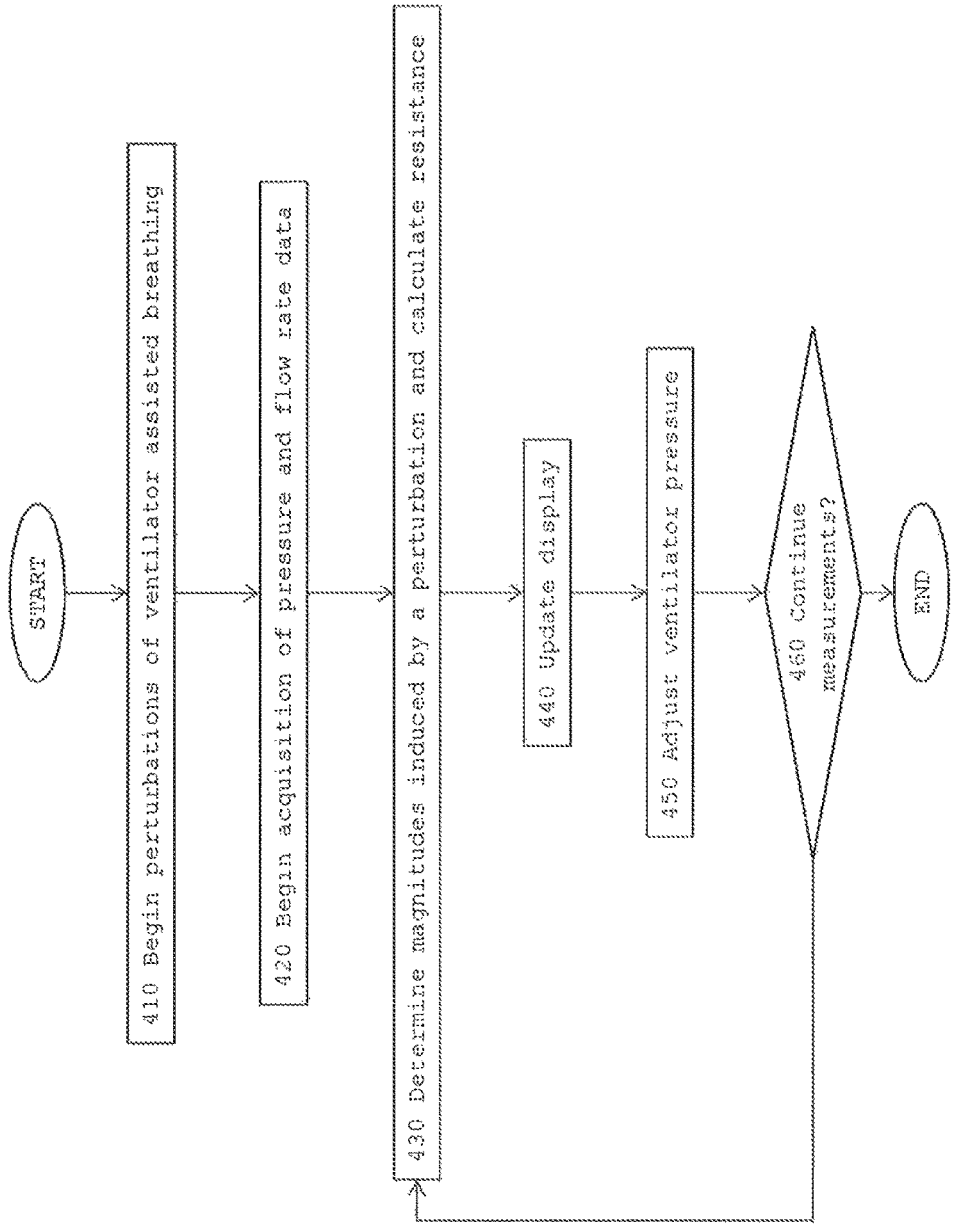

MEASURING RESPIRATORY MECHANICS PARAMETERS OF VENTILATED PATIENTS

CROSS-REFERENCE TO RELATED APPLICATIONS

This application claims the benefit of U.S. Provisional Patent Application No. 62/033,503, titled "Measuring Respiratory Mechanics Parameters of Ventilated Patients" and filed on Aug. 5, 2014, which is incorporated herein by reference in its entirety.

BACKGROUND

Present invention embodiments relate to an airflow perturbation device and techniques for measuring parameters of respiratory mechanics, and more specifically, for measuring respiratory resistance of ventilated patients.

Patients suffering respiratory distress often breathe using a pulmonary ventilation device. A pulmonary ventilation device (or ventilator) breathes for the patient by providing an intermittent high pressure to drive air into the lungs during inhalation and then allowing air to escape from the lungs during exhalation. The patient and ventilator form a closed system not directly in contact with the atmosphere.

Knowledge of the respiratory resistance of the patient during ventilation may be useful because higher resistances require more pressure and time to deliver a given tidal volume of air to the lungs. If ventilator pressure is set too high, then respiratory damage can occur due to lung over inflation. Such damage may disable the patient for the remainder of her or his lifetime. However, conventional approaches to estimating the respiratory resistance of ventilated patients may lack accuracy and do not lend themselves to constant monitoring or distinguish between inspiratory resistance and expiratory resistance.

SUMMARY

According to one embodiment of the present invention, an airflow perturbation device for measuring respiratory resistance of a patient breathing with the use of a. ventilator comprises a sealed housing having a first port and a second port each configured to couple to a ventilator hose, a perturbation mechanism to periodically alter air flow resistance between the first on and the second port, a pneumotachometer comprising a flow sensor to measure airflow between the first port and the second port, a pressure sensor to measure a difference in air pressure between the first port and the second port, and a computing system comprising at least one processor configured to receive data from the flow sensor and pressure sensor. The computing system determines an airflow resistance based on the received data. Embodiments of the present invention further include a method for measuring respiratory resistance of a ventilated patient in substantially the same manners described above.

BRIEF DESCRIPTION OF THE SEVERAL VIEWS OF THE DRAWINGS

Generally, like reference numerals in the various figures are utilized to designate like components.

FIG. 4 is a flow diagram illustrating an example manner of using an airflow perturbation device with a ventilated patient according to an embodiment of the present invention.

DETAILED DESCRIPTION

Figure 1:
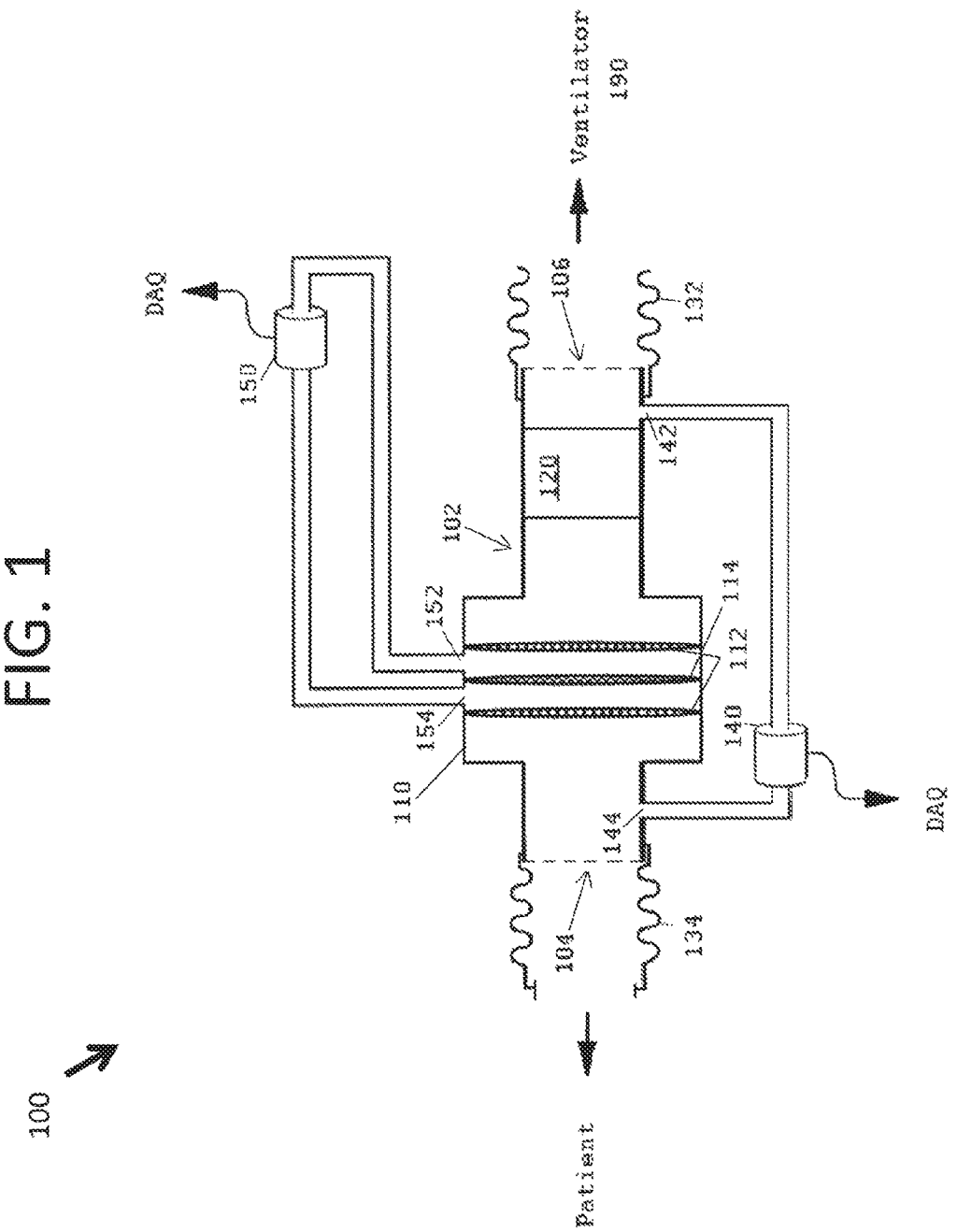
FIG. 1 is a diagrammatic illustration of an example airflow perturbation device for use with ventilated patients according to an embodiment of the present invention.

Present invention embodiments provide an airflow perturbation device and techniques for measuring the respiratory resistance of patients breathing with the use of a ventilator. An airflow perturbation device (APD) measures respiratory resistance internal to a patient by periodically interposing a resistance in the flow path from the patient to the atmosphere. By way of example, this resistance may take the form of a rapidly rotating segmented wheel that intermittently creates a partial obstruction to airflow. When the resistance is in the flow pathway, the patient's breathing flow is reduced by a small amount from the flow that would have existed absent the resistance. The patient's breathing flow may be measured using a pneumotachometer. The presence of the resistance also increases the magnitude both positive and negative, of the pressure measured at the mouth.

The measured changes in airflow and pressure at the mouth produced by the periodically interposed air flow resistance may be used to determine the patient's respiratory resistance, For example, during a time when there is no obstruction, the airflow is described by $$P_A = \dot{V}_{open} \times (R_{resp} + R_{open}) \quad (1)$$

where $$R_{open} = \frac{P_{m,open}}{\dot{V}_{open}}, \quad (2)$$

$P_A$ is respiratory pressure relative to the atmosphere, $\dot{V}_{open}$ is the airflow (e.g., volume of air through the APD per time) with no obstruction, $R_{resp}$ is the respiratory resistance, $R_{open}$ is the resistance of the APD with no obstruction (e.g., the resistance of the pneumotachometer), and $P_{m,open}$ is the mouth pressure with no obstruction.

When there is a partial obstruction (e.g., from the rotating wheel), airflow is described by $$P_A = \dot{V}_{obs} \times (R_{resp} + R_{obs}) \quad (3)$$

where $$R_{obs} = \frac{P_{m,obs}}{\dot{V}_{obs}}, \quad (4)$$

$\dot{V}_{obs}$ is the air flow with a partial obstruction, $R_{obs}$ is the resistance of the flow sensor and the device with a partial obstruction, and $P_{m,obs}$ is the mouth pressure with a partial obstruction.

The equations above yield $$R_{resp} = \frac{P_{m,obs} - P_{m,open}}{\dot{V}_{open} - \dot{V}_{obs}} = \frac{\Delta P}{-\Delta \dot{V}} \qquad (5)$$

The quantities $\Delta P = P_{m,obs} - P_{m,open}$ and $\Delta \dot{V} = \dot{V}_{obs} - \dot{V}_{open}$ are referred to as perturbations. They are calculated based on the peaks or valleys of the actual signals with respect to the signals that would have been present if no perturbation had occurred.

One aspect of a present invention embodiment is an airflow perturbation device capable of operating with a patient and ventilator that are parts of a closed system that is not open to the atmosphere. Such an airflow perturbation device may be referred to as an APDV. According to an embodiment of the present invention, an APDV measures pressure at the mouth relative to pressure at the ventilator output. A pressure tap accesses the pressure at the mouth, and another pressure tap accesses pressure at the ventilator output. Resistance in the flow path from the patient to the ventilator is imposed using a hermetically sealed mechanism.

Other aspects provided by present invention embodiments include a non-invasive, direct measurement of respiratory resistance; a lightweight, portable and inexpensive device; the capability of performing measurements in less than one minute and continuously updating those measurements; measurement of spontaneous breathing that does not require conscious or cooperative patients; separate measurement of inhalation and exhalation resistances; a device that requires no special skill to use; results that are highly reproducible with low variation; measurements that are sensitive to changes in resistance; a device that may be used to give useful resistance measurements from small children; and a device that may be used with animals.

An example airflow perturbation device for use with a ventilated patient (an APDV) according to an embodiment of the present invention is illustrated in FIG. 1. In particular, APDV 100 comprises pneumotachometer 110, perturbation mechanism 120, pressure sensor 140, pressure taps 142 and 144, and flow sensor 150. Ventilation hoses 132 and 134 direct air between the APDV and ventilator 190 and the patient, respectively. Pressure sensor 140 measures the relative pressure between the patient's mouth and the ventilator output via pressure taps 144 and 142. In one embodiment, pressure tap 144 may be disposed at or near the interface between the APDV and ventilation hose 134 to access the pressure at the patient's mouth, and pressure tap 142 may be disposed at or near the interface between the APDV and ventilation hose 132 to access the pressure at the ventilator output. Signals from pressure sensor 140 and flow sensor 150 may be sent to a data acquisition system (DAQ). The entire APDV ensemble is hermetically sealed or substantially sealed against the atmosphere between ventilation hoses 132 and 134. For example, the APDV ensemble may be contained within a sealed housing 102 from which leakage is small (e.g., less than 10%, 1%, etc. of the flow rate through the APDV). The housing may comprise ports 104, 106 for hermetically coupling to the ventilator hoses. As illustrated in the exemplary embodiment of FIG. 1, the sealed housing 102 may have a port 104 coupled to ventilation hose 134 and a port 106 coupled to ventilation hose 132. Ventilation hoses 132 and 134 may be hermetically coupled to the ventilator and patient respectively to form a patient-APDV-ventilator system that is sealed against the atmosphere. Moreover, as is further shown in the exemplary embodiment of FIG. 1, pressure tap 144 may be disposed proximate port 104, while pressure tap 142 may be disposed proximate the second port 106.

Pneumotachometer 110 and flow sensor 150 measure airflow between the patient and ventilator through the APDV. Pneumotachometer 110 comprises airflow resistance 114 (e.g., a fine metal mesh, an array of capillaries, etc.) and may include airflow elements 112 to facilitate laminar airflow across airflow resistance 114. In one embodiment, airflow elements 112 are meshes disposed before and after airflow resistance 114. Pneumotachometer 110 further comprises pressure taps 152 and 154 disposed substantially on the ventilator side and patient side, respectively, of airflow resistance 114. Flow sensor 150 may be implemented using a differential pressure sensor to measure the difference in pressure across airflow resistance 114 using pressure taps 152 and 154. This pressure difference is related to the airflow across airflow resistance 114, The pressure-airflow relationship may be modeled as a proportional or linear relationship, and may be calibrated using standard techniques.

Aspects of the device may operate in manners similar to corresponding aspects described in U.S. Pat. No. 6,066,101, which is hereby incorporated by reference in its entirety.

Figure 2B:
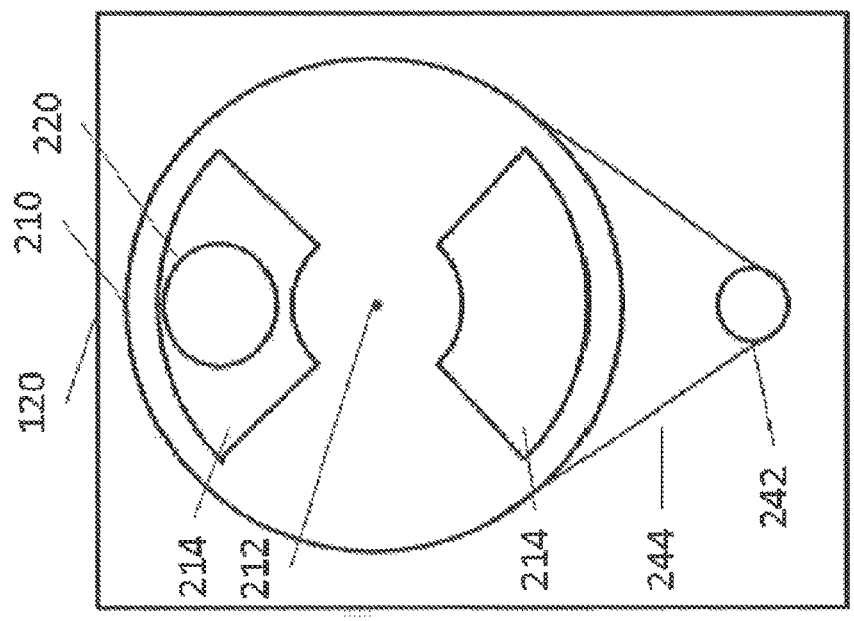
FIGS. 2A and 2B are block diagrams of an example perturbation mechanism in cross-sectional side-view and front view respectively according to an embodiment of the present invention.
Figure 2A:
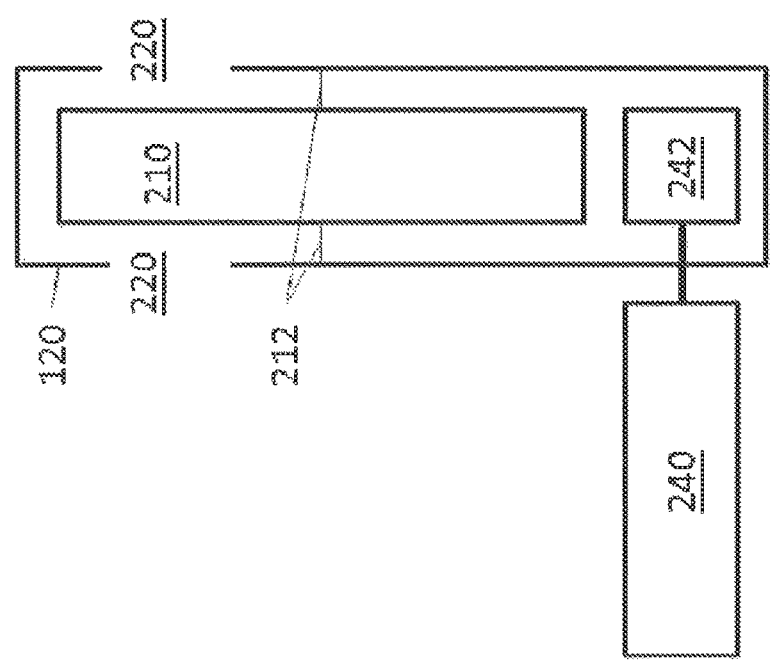

An example perturbation mechanism 120 is illustrated in FIGS. 2A and 2B in cross-sectional side-view and front view, respectively, according to an embodiment of the present invention. In particular, the perturbation mechanism may comprise wheel 210 disposed between opposing apertures 220. Air flowing between the patient and ventilator passes into perturbation mechanism 120 through a first aperture 220, across wheel 210, and out of perturbation mechanism 120 through a second aperture 220. Wheel 210 is rotatable about shaft 212 and comprises regions of different airflow resistance such that the rotating wheel presents periodically varying resistance to the airflow between the patient and ventilator. For example, wheel 210 may comprise a screen containing at least one open region 214 having a size and location to substantially cover apertures 220 during a portion of the wheel's rotation. Alternatively, region 214 may be screened and the remainder of the wheel may be substantially open or have a screen of another gauge than region 214 to provide a different airflow resistance. In either case, should the perturbation mechanism fail, there will still be a pathway for flow from the ventilator to the patient, even if this pathway has a higher resistance than normal. The ventilator will still be capable of air delivery because the APDV never completely obstructs flow. In this respect, the APDV is fail-safe.

Rotation of wheel 210 may be driven by motor 240, using pulley 242, and drive belt 244. Motor 240 may be contained within the sealed APDV housing. Power for the motor may be supplied by batteries residing within the housing. Alternatively, the APDV housing may be sealed around a pass-through for a power chord to provide power from an external source.

In alternative embodiments, perturbations to the airflow may be produced in a manner other than with a wheel (for instance, by pinching a tube or using a shutter). In an embodiment using a pinching mechanism, the mechanism may be configured to pinch a tube at most partly closed in order ensure a pathway in the event mechanism fails. A pinching mechanism may be implemented using an electrical function generator and electro-sensitive materials that contract as applied voltage increases, or in any other electrical or mechanical manner. In an embodiment using a shutter mechanism, the shutters may be implemented using screens to avoid complete blockage of the airflow. In any embodiment, the perturbation mechanism may include a plurality (e.g., two, three, etc.) of pathways (e.g., tubes), of which fewer than all are perturbed (e.g., pinched or obstructed by a shutter or wheel).

Figure 3:
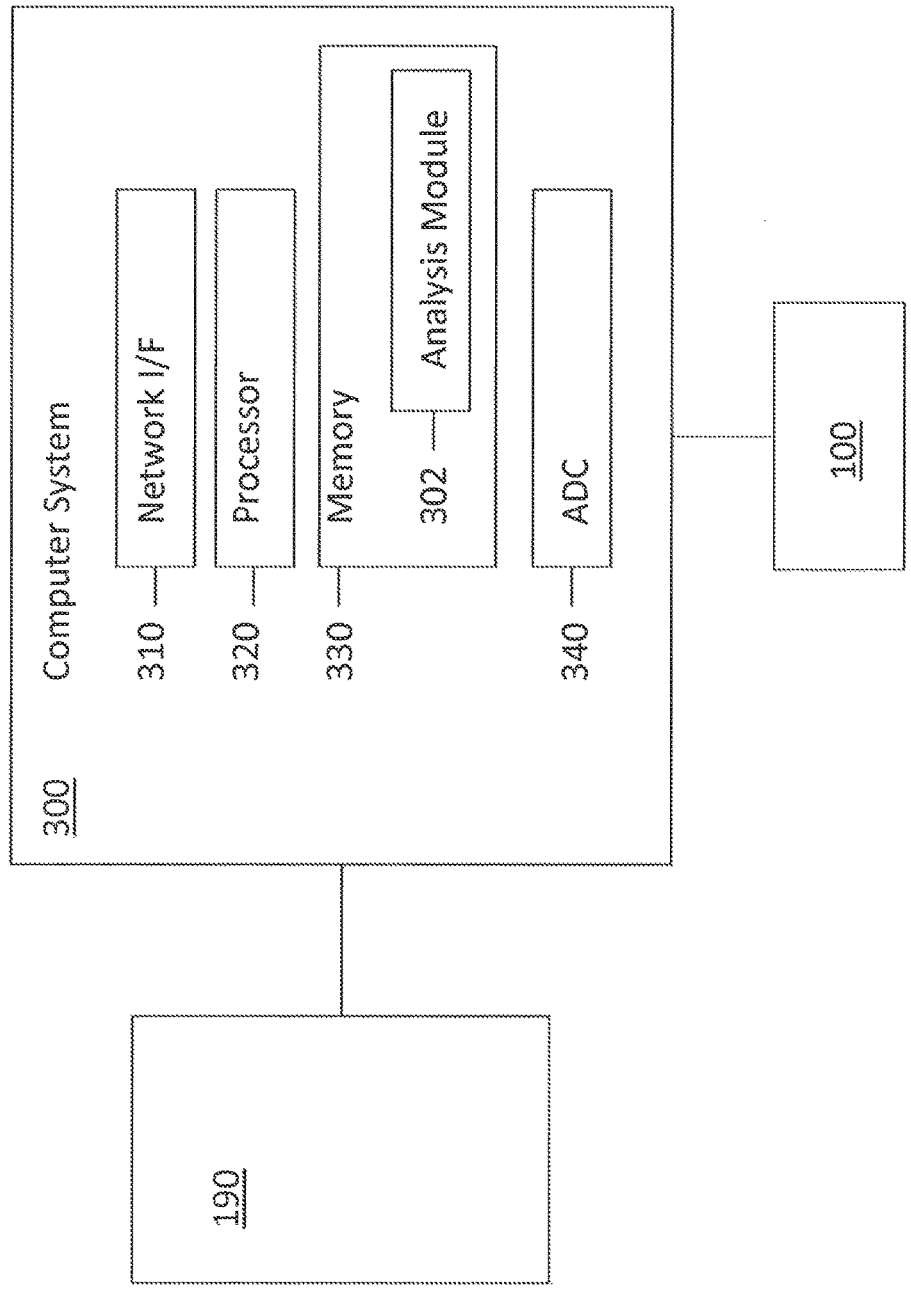
FIG. 3 is a block diagram of an example computing system for data acquisition and analysis according to an embodiment of the present invention.

An example computing system for data acquisition and analysis according to an embodiment of the present invention is illustrated in FIG. 3. In particular, computing system 300 may be implemented by a conventional or other computer system preferably equipped with a display or monitor, a base (es., including at least one processor 320, memories 330, analog-to-digital converter (ADC) 340, and/or other external or internal network interface or communications devices 310 (e.g., modem, network cards, etc.)), optional input devices (e.g., a keyboard, mouse, or other input device), and any commercially available and custom software (e.g., analysis module 302 software, ADPV driver software, ventilator control software, database software etc.)).

Analysis module 302 may include one or more modules or units (e.g., ApplyCalibration module, FindPerturbations module, GetVirtualData module, CalcResistance module, Display module, Control module, etc.) to perform the various functions of present invention embodiments described below (es., calibrating transducer signals, detecting begin and end points of perturbations, interpolating between perturbation begin and end points, calculating respiratory resistance, adjusting ventilator pressure, etc.), may be implemented by any combination of any quantity of software and/or hardware modules or units, and may reside within memory 330 of computing system 300 for execution by processor 320. The analysis module may be implemented across plural computing systems. The computing system(s) may present any graphical user (e.g., GUI, etc.) or other interface (e.g., command line prompts, menu screens, etc.) to receive commands from users and interact with the analysis module, APDV, and/or other modules, devices, or services.

Computing system 300 communicates with APDV 100 to receive signals from pressure sensor 140 and flow sensor 150, and may communicate with ventilator 190 and/or other systems (e.g., database systems, client systems, server systems, etc.) over a network implemented by any number of any suitable communications media (e.g., wide area network (WAN), local area network (LAN), Internet, intranet, etc.). Computing system 300 may utilize any local or remote data sources implemented by any conventional information storage system (e.g., relational database, file system server, etc.).

Figure 5A:
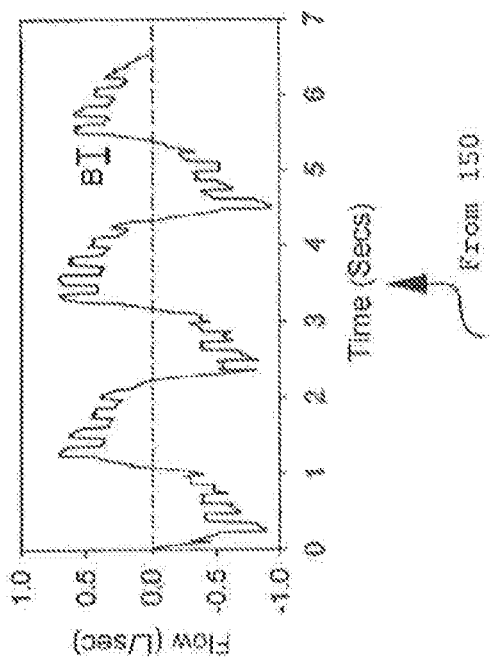
FIGS. 5A and 5B are illustrations of example mouth pressure and flow signals respectively according to an embodiment of the present invention.
Figure 5B:
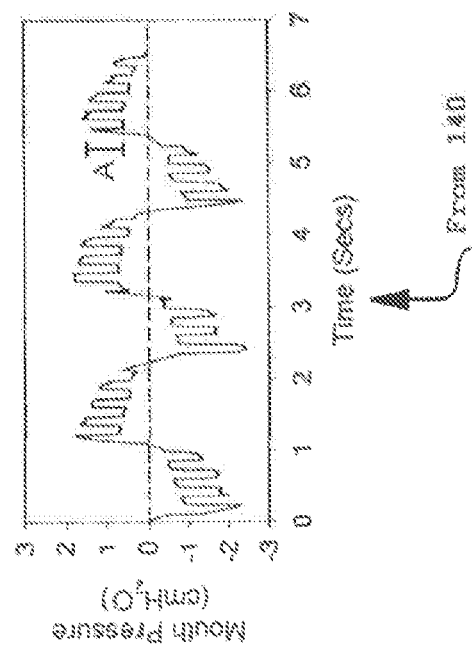
Figure 6:
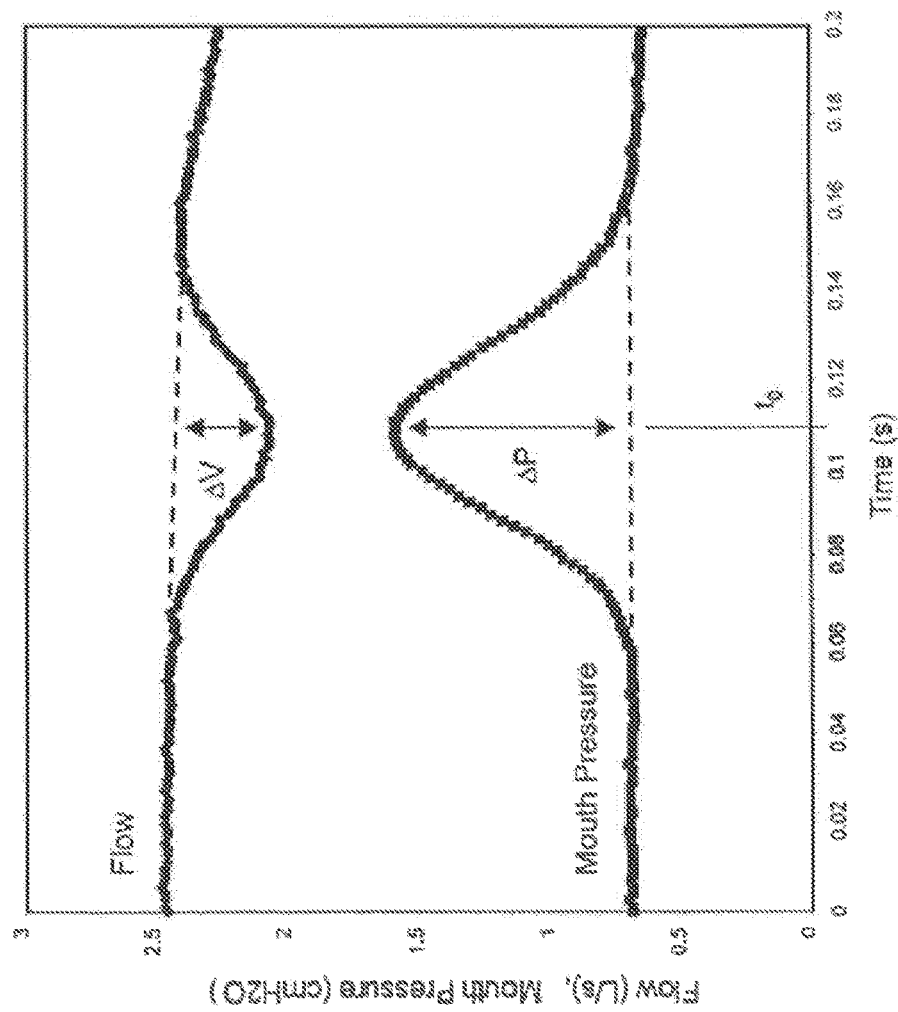
FIG. 6 is an illustration of example pressure and flow signals for an individual perturbation according to an embodiment of the present invention.

An example manner of determining airflow resistance of a ventilated patient to regulate ventilator pressure according to an embodiment of the present invention is illustrated in FIGS. 4-6. Perturbations of ventilator assisted breathing are initiated at step 410. Ventilator hose 134 is secured to the patient. Ventilator hose 132 is secured to the ventilator. The ventilator is activated, and the patient breathes with the assistance of the ventilator. The perturbation mechanism is activated, e.g., by engaging power to motor 240.

At step 420, acquisition of pressure and flow rate data begins. The pressure transducers of pressure sensor 140 and flow sensor 150 send electric signals to computer system 300. ADC 340 digitizes the signals. Analysis module 302 continually monitors and records the digitized signals from the pressure transducers for mouth pressure and pneumotachometer flow sensor. The analysis module may apply predetermined calibrations to the data (e.g., converting digitized pressure transducer data from pressure sensor 140 to units of pressure, converting digitized pressure transducer data from flow sensor 150 to units of volume per time based on a measured resistance of airflow resistance 114, etc.). Example data from pressure sensor 140 and flow sensor over time are illustrated in FIGS. 5A and 5B, respectively. The larger period structure corresponds to the patient's breathing. The perturbation mechanism induces the smaller timescale structure; the resulting changes in the mouth pressure may have a typical magnitude indicated by A, and the changes in the air flow may have a typical magnitude indicated by B.

At step 430, analysis module 302 determines the pressure and flow changes due to an individual perturbation and performs a calculation of the respiratory resistance based on those changes. Typically, the analysis module operates in real-time. Example mouth pressure and air flow data for an individual perturbation are illustrated in FIG. 6. The analysis module interpolates (e.g., linearly) the mouth pressure and flow rate data between the points when the signals are essentially unperturbed (e.g., when the wheel resistance is zero) immediately preceding the perturbation and immediately following the perturbation. These interpolated signals are referred to as virtual signals and are indicated by the dashed curves in FIG. 6. Changes in mouth pressure and flow rate induced by the perturbation mechanism are measured with respect to the corresponding virtual signals. In particular, the changes may be computed as the observed signal minus the virtual signal. The analysis module determines the time ($t_0$) at which the magnitudes of the changes are greatest. The pressure change ($\Delta P$) and flow change ($\Delta \dot{V}$) at $t_0$ may be used to calculate respiratory resistance using Eq. 5. These data may be separated, based on flow signal polarity, into resistance during inspiration and resistance during expiration. This separation can be useful for determining abnormalities that affect one or another of the breathing phases.

At step 440, the analysis module may update the display to indicate the calculated respiratory resistance.

At step 450, the ventilator pressure may be adjusted in response to the respiratory resistance calculation. That is, output from the APDV may be used to control ventilator pressure. Because the APDV may be used as a continuous respiratory resistance monitor, it may be used to increase ventilator pressure during phases of breathing when respiratory resistance is high and decrease ventilator pressure when respiratory resistance is low. Such a ventilator control can be beneficial for patient recovery.

At step 460, the analysis module determines whether to continue analyzing signal data, For example, if the analysis module is halted by a user, processing may end. Otherwise, processing returns to step 430, and the next perturbation is detected and analyzed. Respiratory resistance is normally calculated once for each perturbation.

It will be appreciated that the embodiments described above and illustrated in the drawings represent only a few of the many ways of implementing embodiments for measuring respiratory resistance of a ventilate patient.

An embodiment of the present invention may utilize any conventional or other pneumotachometer technology, pressure sensors, and perturbation mechanism (e.g., rotary wheel, shutter, pinch techniques, etc.), Any type of ventilator and ventilator hoses may be used.

The environment of the present invention embodiments may include any number of computer or other processing systems (e.g., client or end-user systems, server systems, etc.) and storage systems (e.g., file systems, databases, or other repositories), arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., database software, communications software, etc.). These systems may include any types of monitors and input devices (e.g., keyboard, mouse, voice recognition, touch screen, etc.) to enter and/or view information.

It is to be understood that the software of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM. DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) fix obtaining or providing information, where the interface may include any information arranged in any fashion. The interface may include any number of any types of input or actuation mechanisms (es., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

What is claimed is:

1. A system for measuring respiratory resistance of a subject breathing with use of a ventilator comprising:
    an airflow perturbation device comprising:
        a sealed housing having an airflow path, a first port at one end of the path, and a second port at an opposite end of the path, each configured to couple to a ventilator hose, wherein the housing is sealed against the atmosphere;
        a perturbation mechanism positioned within the airflow path between the first and second ports, wherein the perturbation mechanism includes an element disposed in the airflow path and an actuator coupled to the element to control the element to intermittently create an obstruction to airflow and periodically alter airflow resistance between the first port and the second port;
        a pneumotachometer comprising a flow sensor, a first pressure tap disposed proximate the first port and a second pressure tap disposed proximate the second port to measure airflow between the first port and the second port;
        a pressure sensor to measure a difference in air pressure between the first port and the second port, wherein the pressure sensor is coupled to the first pressure tap to access pressure at a position between a mouth of the subject and the perturbation mechanism, and to the second pressure tap to access pressure at a position between the perturbation mechanism and the ventilator; and
    a computing system comprising at least one processor configured to:
        receive data from the flow sensor and pressure sensor; and
        determine an airflow resistance based on the received data.

2. The system of claim 1, wherein a first ventilation hose is hermetically coupled to the first port and to the subject and a second ventilation hose is hermetically coupled to the second port and to the ventilator.

3. The system of claim 1, wherein the airflow resistance is determined in less than a minute from initiating operation of the airflow perturbation device.

4. The system of claim 1, wherein determining the airflow resistance comprises continuously updating the determined airflow resistance.

5. The system of claim 1, wherein the perturbation mechanism at most partly obstructs the airflow path between the first and second ports.

6. The system of claim 1, wherein the airflow perturbation device controls the ventilator to adjust pressure provided by the ventilator in response to the determined airflow resistance.

7. The system of claim 1, wherein the perturbation mechanism comprises a pinching mechanism configured to pinch a flexible tube using a generator and a contractable tube.

8. The system of claim 1, wherein the perturbation mechanism comprises a rotating segmented wheel.

9. The system of claim 1, wherein the perturbation mechanism comprises a shutter.

10. The system of claim 1, wherein determining the airflow resistance comprises determining changes in pressure and airflow with respect to corresponding pressure and airflow expected in the absence of the alteration to the air flow resistance.

11. The system of claim 10, wherein the changes in the pressure and airflow expected in the absence of the alteration are determined by interpolating signals between perturbations.

12. A method of measuring respiratory resistance of a subject breathing with use of a ventilator comprising:
periodically perturbing airflow resistance between a first port and a second port of a sealed housing via a perturbation mechanism, wherein the first port is coupled to the subject via a first ventilator hose, and the second port is coupled to a ventilator via a second ventilator hose, wherein the sealed housing includes an airflow path, a first port at one end of the path, and a second port at an opposite end of the path, each configured to couple to a ventilator hose, wherein the housing is sealed against the atmosphere, and wherein the perturbation mechanism is positioned within the airflow path between the first and second ports and includes an element disposed in the airflow path and an actuator coupled to the element to control the element to intermittently create an obstruction to airflow and periodically alter airflow resistance between the first port and the second port;
measuring airflow between the first port and the second port using a pneumotachometer having a flow sensor, a first pressure tap disposed proximate the first port and a second pressure tap disposed proximate the second port;
measuring a difference in air pressure between the first port and the second port using a pressure sensor, wherein the pressure sensor measures a difference in air pressure between the first port and the second port, wherein the pressure sensor is coupled to the first pressure tap to access pressure at a position between a mouth of the subject and the perturbation mechanism, and to the second pressure tap to access pressure at a position between the perturbation mechanism and the ventilator;
receiving data from the flow sensor and pressure sensor at a computing system comprising at least one processor; and
determining, via the at least one processor, an airflow resistance based on the received data.

13. The method of claim 12, further comprising:
coupling the system to an unconscious subject; and
measuring the respiratory resistance of the unconscious subject.

14. The method of claim 12, further comprising:
coupling the system to a non-human subject; and
measuring the respiratory resistance of the non-human subject.

15. The method of claim 12, further comprising adjusting pressure provided by the ventilator in response to the determined airflow resistance.

16. The method of claim 12, wherein periodically perturbing the airflow resistance comprises rotating a segmented wheel between the first and second ports.

17. The method of claim 12, wherein periodically perturbing the airflow resistance comprises a selected one of operating a shutter between the first and second ports and pinching a tube between the first and second ports.

18. The method of claim 12, wherein determining the airflow resistance comprises determining changes in pressure and airflow with respect to corresponding pressure and airflow expected in the absence of perturbation.

19. The method of claim 18, wherein the changes in the pressure and airflow expected in the absence of perturbation are determined by interpolating signals between perturbations.

* * * * *